(12) United States Patent
Roskopf et al.

(10) Patent No.: US 8,585,716 B2
(45) Date of Patent: Nov. 19, 2013

(54) APPARATUS FOR APPLYING HEMOSTATIC CLIPS

(75) Inventors: William R. Roskopf, Pleasanton, CA (US); Antoine Papoz, Le Chesnay (FR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1221 days.

(21) Appl. No.: 11/870,800

(22) Filed: Oct. 11, 2007

(65) Prior Publication Data

US 2008/0147093 A1 Jun. 19, 2008

Related U.S. Application Data

(60) Provisional application No. 60/874,930, filed on Dec. 13, 2006.

(51) Int. Cl.
*A61B 17/00* (2006.01)
*A61B 18/18* (2006.01)

(52) U.S. Cl.
USPC .............................................. 606/143; 606/41

(58) Field of Classification Search
USPC ......... 606/27, 41, 142, 143, 139, 108, 40, 46, 606/47, 49–52; 24/341, 560, 564, 710.8; 29/812
See application file for complete search history.

(56) References Cited

U.S. PATENT DOCUMENTS

| 4,227,279 | A | * | 10/1980 | Tribolet ........................... 15/321 |
| 5,201,691 | A | * | 4/1993 | Doyle ............................... 475/53 |
| 5,207,691 | A | * | 5/1993 | Nardella ........................ 606/142 |
| 5,542,949 | A | * | 8/1996 | Yoon .............................. 606/143 |
| 5,582,611 | A | | 12/1996 | Tsuruta et al. |
| 7,128,747 | B2 | * | 10/2006 | Ginn .............................. 606/108 |
| 2003/0036755 | A1 | | 2/2003 | Ginn |
| 2005/0072827 | A1 | | 4/2005 | Mollenauer |
| 2005/0216036 | A1 | * | 9/2005 | Nakao ........................... 606/142 |
| 2008/0147092 | A1 | * | 6/2008 | Rogge et al. .................. 606/142 |

FOREIGN PATENT DOCUMENTS

DE 100 11 292 9/2000
WO 94/24949 11/1994

* cited by examiner

*Primary Examiner* — Tuan V Nguyen
(74) *Attorney, Agent, or Firm* — Fay Kaplun & Marcin, LLP

(57) ABSTRACT

An apparatus includes a hemostatic clip assembly including at least one hemostatic clip, a first one of the at least one hemostatic clips having a tissue clamp movable between a tissue receiving configuration and a tissue clamping configuration and a deployment mechanism deploying a distal most one of the clips onto target tissue and a cautery apparatus applying energy to the distal most one of the clips to cauterize the target tissue.

9 Claims, 3 Drawing Sheets

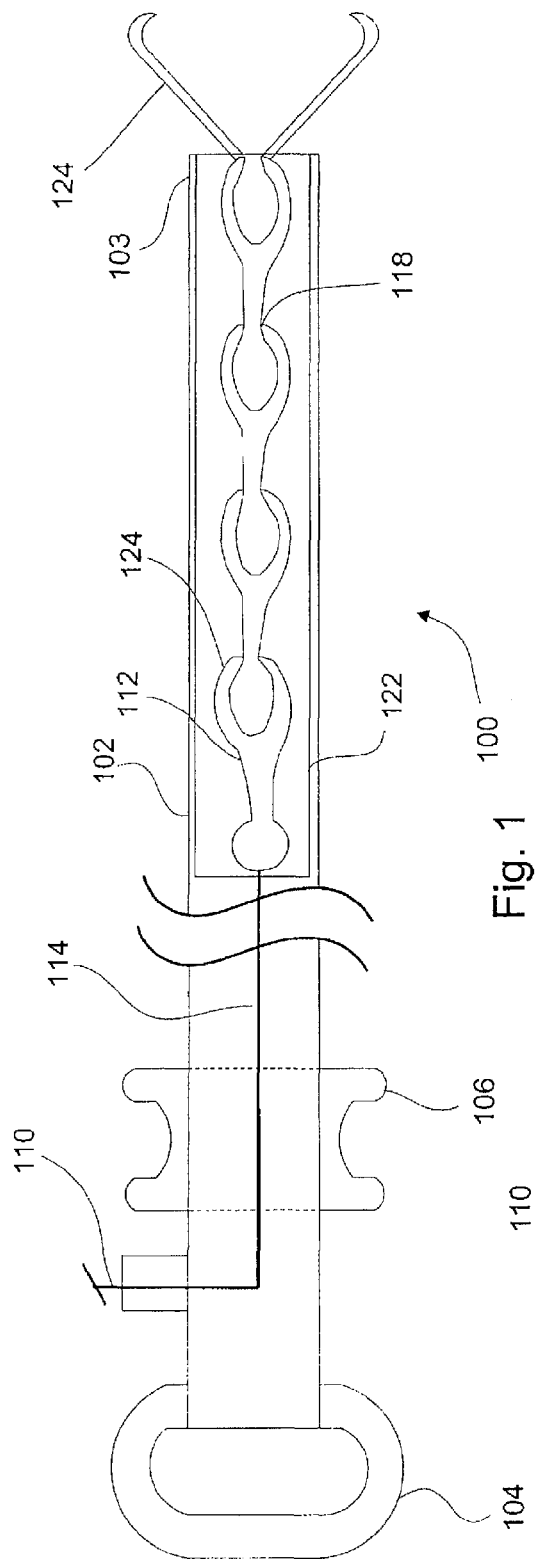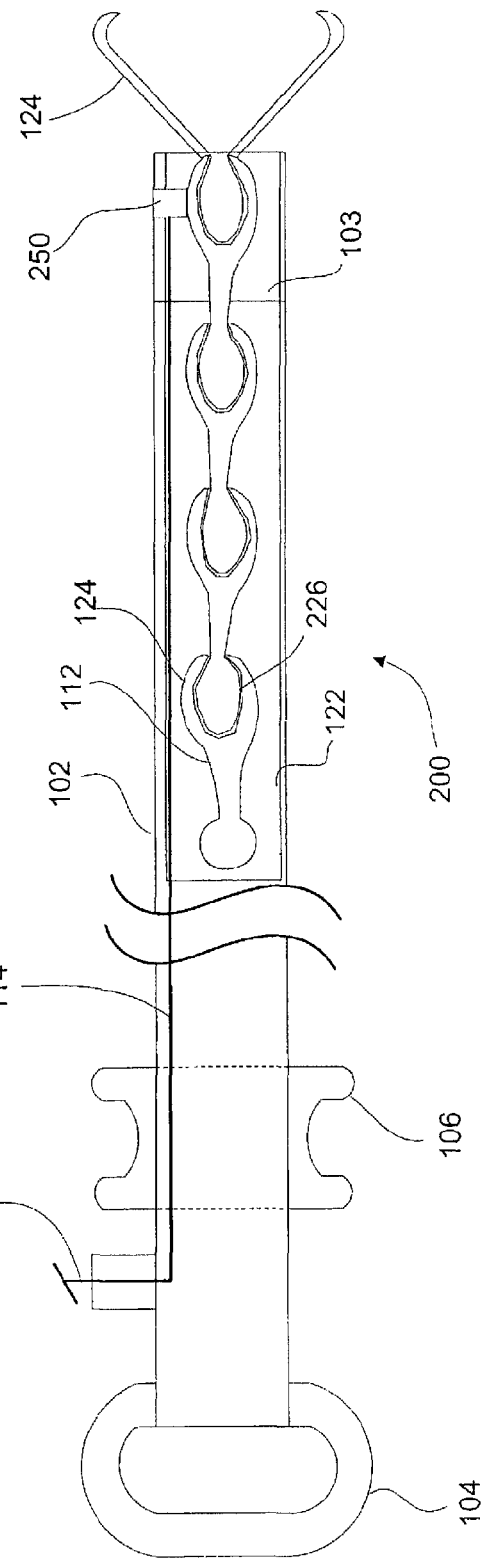

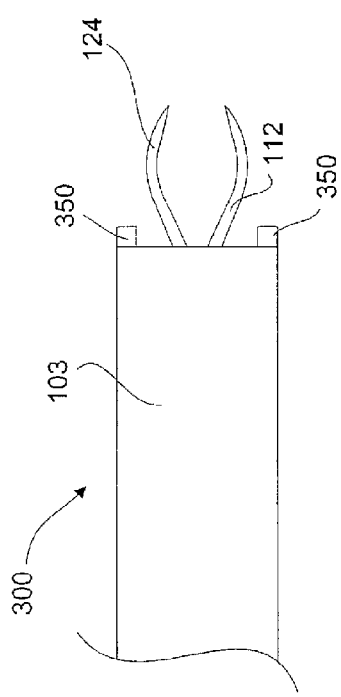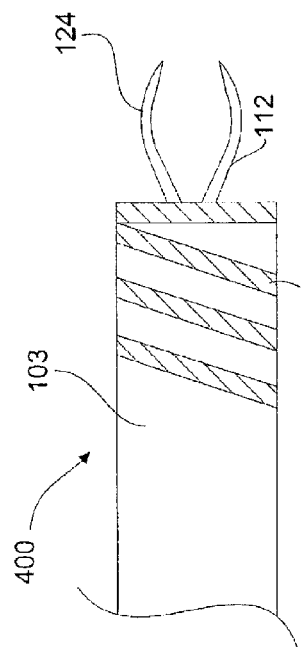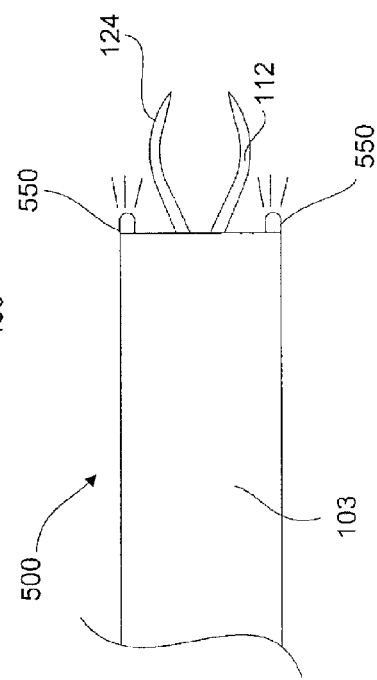

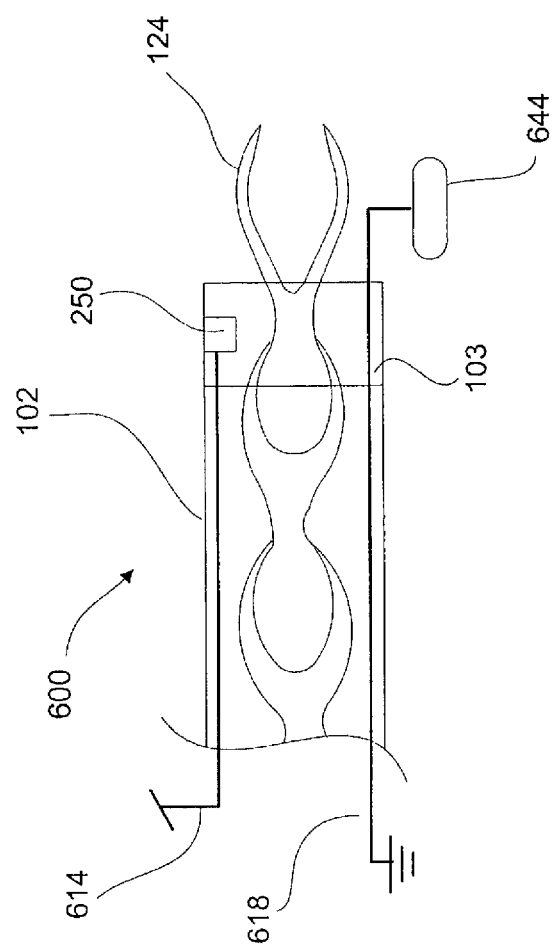

APPARATUS FOR APPLYING HEMOSTATIC CLIPS

PRIORITY CLAIM

This application claims the priority to the U.S. Provisional Application Ser. No. 60/874,930, entitled "Apparatus for Applying Hemostatic Clips," filed Dec. 13, 2006. The specification of the above-identified application is incorporated herewith by reference.

BACKGROUND

Hemostatic clipping tools have been endoscopically inserted to treat internal bleeding. These clipping tools deploy hemostatic clips which clamp edges of a wound together. After a number of clips sufficient to clamp all of the target sites (i.e., bleeding wounds) has been deployed, the tool is withdrawn from the body.

Internal bleeding is also treated by applying heat to tissue to cause rapid coagulation of the bleeding vessels (i.e., cauterizing). Cauterizing is particularly applicable to bleeding sites with edges relatively close to one another.

SUMMARY OF THE INVENTION

In one aspect, the present invention is directed to an apparatus, comprising a hemostatic clip assembly comprising at least one hemostatic clip, a first one of the at least one clips having a tissue clamp movable between a tissue receiving configuration and a tissue clamping configuration and a deployment mechanism deploying a distal most one of the clips onto target tissue and a cautery apparatus heating the distal most one of the clips to cauterize the target tissue.

In another aspect, the present invention is directed to a method comprising advancing through an endoscope positioned within a body lumen a hemostatic clip deployment device to reach a target bleeding site, the clip deployment device including at least one hemostatic clip therein and providing electric power to a first one of the at least one hemostatic clips, wherein the first hemostatic clip is a distal most one of the hemostatic clips in combination with cauterizing a target portion of tissue with the first hemostatic clip and deploying the first hemostatic clip onto the target tissue to mechanically clamp the target tissue.

BRIEF DESCRIPTION OF THE DRAWINGS

FIG. 1 is a schematic side view of a clipping device according to a first embodiment of the present invention.

FIG. 2 is a schematic side view of a clipping device according to a second embodiment of the present invention.

FIG. 3 is a schematic side view of a clipping device according to a third embodiment of the present invention.

FIG. 4 is a schematic side view of a clipping device according to a fourth embodiment of the present invention.

FIG. 5 is a schematic side view of a clipping device according to a fifth embodiment of the present invention.

FIG. 6 is a schematic side view of a clipping device according to a sixth embodiment of the present invention.

DETAILED DESCRIPTION

Endoscopic hemostatic clipping devices are designed to reach target tissues deep within the body (e.g., within the GI tract, the pulmonary system, the vascular system or within other lumens and ducts). During procedures to treat those areas, an endoscope is generally used to provide access to and visualization of the target tissue with the clipping device introduced, for example, through a working channel of the endoscope.

In many situations (e.g., larger wounds) a single hemostatic clip is insufficient to stop the bleeding and multiple hemostatic clips are applied to a wound. The application of multiple clips with conventional single applicators is difficult and time consuming as, after each clip is applied, the applicator must be withdrawn, reloaded and reinserted to the desired location before another clip can be applied. Thus, multi-clip applicators have been developed which are not required to be withdrawn, reloaded and re-inserted after each clip is deployed. These devices contain a plurality of hemostatic clips, that can be deployed sequentially with minimal movement of the applicator within the body.

The embodiments of the present invention provide for methods and devices which enhance the treatment of internal bleeding as compared to the use of hemostatic clips alone. In particular, the present invention provides a multi-clip deployment mechanism combining mechanical pressure (e.g., from clips) with cauterization. More specifically, embodiments of the exemplary system combine electrical or thermal excitement of target tissue to cauterize damaged blood vessels with a multi-clip deployment mechanism mechanically clamping the wound closed. As described above, the multi-clip deployment device can deploy multiple clips without being removed from the body for reloading.

As shown in FIG. 1, a combination multi-clip deployment/cauterization device 100 comprises a flexible elongated body or shaft 102 dimensioned to pass through the working channel of an endoscope to a target site within the body. The device 100 is advanced into the working channel until a distal end 103 thereof reaches the source of the bleeding. The manipulation and visualization tools of the endoscope may be used in this step to assist in correctly placing the distal end 103 in a desired relation to the target tissue.

The device 100 is designed to deploy multiple clips to a target region without having to be withdrawn from the endoscope to reload hemostatic clips. A clip magazine 122 formed in the elongated portion 102 of the device 100 stores therein multiple hemostatic clips 112 for deployment from the distal end 103. In an exemplary embodiment, the clips 112 are stored in the magazine 122 in a folded storage configuration. As will be understood by those of skill in the art, each of the clips 112 comprises arms 124 that open during deployment from the distal end 103 and then lock in a clamping configuration gripping the target tissue. The clips 112 may be shaped to optimize hemostatis and/or energy conductivity. For example, a surface area of the arms 124 may be textured to enhance grip. The surface area may also be increased to allow for increased tissue contact and decreased electrical resistance, thus enhancing energy delivery.

A handle 104 may be incorporated in the device 100 to facilitate its manipulation and a spool 106 or other actuator may be disposed slidably on the elongated portion 102. The spool 106 is moved along the length of the elongated portion 102 to deploy the hemostatic clips 112. As will be understood by those of skill in the art, a deployment mechanism (not shown) connects the spool 106 and the hemostatic clips 112 so that, as the user moves the spool 106, the deployment mechanism deploys the distal most hemostatic clip 112 to clamp the target tissue.

While contacting the target tissue, the hemostatic clip 112 transfers energy to the tissue to cauterize the wound. For example, a proximal most one of the hemostatic clips 112 may be coupled to a source of electrical energy with each of the clips 112 connected to the adjacent proximal and distal clips 112 to form a chain 130 through which the electrical energy travels. When the most distal hemostatic clip 112 is deployed on target tissue and before it is separated from the chain of clips 112, electrical energy applied to the proximal most clip 112 via a lead 114 travels through all of the intervening clips 112 to the distal most clip 112 to run through the arms 124 of the distal most clip 112 into the tissue gripped thereby to cauterize this tissue. A negligible amount of heat is generated in the more proximal clips as the energy travels therethrough while heat sufficient to ablate is generated at the interface between the distal most clip 112 and the tissue.

In the exemplary embodiment, a cautery connector 110 connects an electric power supply to the device 100 and the lead 114 carries the electrical energy from the connector 110 to the proximal most clip 112. The clips are made of an electrically conductive material, such as metal which forms an electric connection to the arms 124 of the most distal clip 112. For example, electric connections 118 are formed between successive hemostatic clips 112 aligned within the magazine 122. An electric lead 114 may be used to electrically connect the clips 112 to the cautery connection 110. The lead 114 may be an insulated wire, a metal strip, or any other electrically conductive arrangement coupled to the proximal most clip. In other embodiments, the lead 114 may be a conductive tube disposed within a lumen of the elongated body 102. The tube may be separated from an inner surface of the elongated body 102 by an insulating material or coaxially suspended so that air functions as a dielectric layer between the tube and the elongated body 102.

FIG. 2 shows an exemplary embodiment of a deployment/cauterization device 200 in which the lead 114 is coupled to the distal most clip 112. The lead 114 extends along the body 102 of the device 200 towards an electrical contact 250 located at the distal portion 103. An electrical connection is formed with the distal most clip 112, which may be directly or indirectly coupled to the contact 250. For example, each clip 112 may have a corresponding a corresponding contact located along a body portion thereof. An inner surface of the distal portion 103 may be electrically insulated to prevent transfer of electrical energy from the contact 250 to the body 102. Each of the plurality of clips 112 may include an insulating layer 226 along an inner surface of the arms 124. Thus, the clips 112 are electrically isolated from each other and the electrical energy is confined to the distal most clip 112. As each clip 112 moves to the distal portion 103, the clip 112 engages the contact 250 and tissue is clamped between the arms 124. Then, the user switches power on and electrical energy is transmitted through the lead 114 into the distal most clip 112 via the contact 250 to flow through the arms 124 and the tissue gripped thereby. Once cauterization is completed, the distal most clip 112 is released and a subsequent clip 112 is advanced into the distal portion 102. Thus, electrical energy may be applied to each clip 112 individually.

FIG. 3 shows an exemplary embodiment of a deployment/cauterization device 300 in which thermal energy is supplied through the distal portion 103 of the device 300. The device 300 includes one or more heating elements 350 located proximal to the arms 124 of the distal most clip 112. Tissue gripped by the arms 124 is contacted by the heating elements 350 and is cauterized as a result of heat generated thereby. The heating elements 350 may be formed of any electrically resistive material which heats when electrical energy is applied thereto. The distal portion 103 may also be thermally insulated to prevent dispersal of heat into the body 102. Electrical energy may also be applied to the clips 112, which may also be fabricated from, contain or be coated with a material that heats up when electrical energy is applied thereto.

FIG. 4 shows an exemplary embodiment of a deployment/cauterization device 400 in which electrical energy is supplied through an electrically conductive surface of the distal portion 103. The surface may comprise one or more coils 450 wrapping around the exterior of the distal portion 103. The coils 450 are preferably formed of a highly conductive material such as gold or copper. In this embodiment, a proximal most coil 450 may extend into the body 102 to contact the electrical lead 114 (not shown). Alternatively, the coils 450 may be coupled to an external lead. Cauterization may be performed as soon as a sufficient amount of tissue is prepared by clipping. This may occur as early as after the deploying the first distal most clip 112.

FIG. 5 shows an exemplary embodiment of a deployment/cauterization device 500 in which optical energy is delivered via one or more optical elements 550. The optical elements 550 may, for example, be light-emitting diodes that deliver semi-coherent light of a predetermined wavelength and intensity to the tissue. In another embodiment, the optical elements 550 may be fiber optic elements delivering laser light to the tissue. Optical energy delivered in this manner impinges on the target tissue, generating sufficient heat to cauterize the tissue.

FIG. 6 shows an exemplary embodiment of a deployment/cauterization device 600 which includes an active electrical lead 614 and a grounded lead 618. The active lead 614 may be coupled to the contact 250, which delivers electrical energy to the tissue via the distal portion 103. The grounded lead 618 may be coupled to a grounding pad 644 located external to the body 102 of the device 600. The grounding pad 644 may be applied to the patient's body to attract electrical energy from the active lead 614. That is, once the grounding pad 644 is secured to the patient, an electrical circuit is established in which current travels from the active lead 614 through the patient's body and back to the device 600 via the grounded lead 618. The grounding pad 644 may be placed external to the body (e.g., the patient may rest on the pad 644) or, alternatively, may be internally collocated with the clips 112 to contact the tissue.

The present invention is directed to a hemostatic apparatus including a hemostatic clip assembly, a deployment mechanism and an energy delivery apparatus. The clip assembly comprises at least one hemostatic clip, wherein a first one of the at least one hemostatic clips has a tissue clamp movable between a tissue receiving configuration and a tissue clamping configuration. The clips may comprise a chain received in a magazine of the hemostatic apparatus, with each clip coupling to an adjacent clip. The deployment mechanism functions to deploy a distal most one of the clips onto target tissue. The energy delivery apparatus cauterizes target tissue by delivering to tissue energy comprising at least one of thermal, electrical and optical energy. The energy may be transmitted to a target portion of tissue via a distal most clip or a distal portion of the deployment mechanism via an electric element of the energy delivery apparatus. The electric element may transmit energy directly to the distal most clip by coupling thereto or, alternatively, indirectly through the chain of clips by coupling to at least one proximal clip. The deployment mechanism is coupled to a user operated actuator commanding deployment of the distal most clip and may operate concurrently with the delivery apparatus to provide combination therapy.

The energy may also be delivered through a distal portion of the body of the hemostatic apparatus. Electrical energy may be transmitted directly to the target tissue through the distal portion or converted to thermal energy using an electrically resistive element such as the distal most clip, a separate heating element or the distal portion itself. Thermal energy may also be transmitted indirectly by at least one optical element such as a light-emitting diode or a laser that generates optical energy of sufficient intensity to heat the target tissue.

The present invention is also directed to a method including the step of advancing through an endoscope positioned within a body lumen a hemostatic clip deployment device to reach a target bleeding site, the clip deployment device including at least one hemostatic clip therein. The method further includes the steps of providing energy to one of a distal portion of the clip deployment device and a first distal most one of the clips; and cauterizing a target portion of tissue by delivering the energy via at least one of the first hemostatic clip, a separate energy delivery element and a distal portion of the deployment device itself. The method also includes the step of deploying the first hemostatic clip onto the target tissue to mechanically clamp the target tissue. After the first hemostatic clip has been deployed, it may be released so that a second hemostatic clip may be deployed by advancing the second clip to the distal most position. Before deployment of the first clip, the second clip may be coupled to a proximal end of the first clip. The method may include the step of providing electric power to the second clip for transmission therethrough to the first clip. The clip deployment device may include a plurality of hemostatic clips stored in a chain in a magazine. In this embodiment, the method may include the step of providing energy to the first clip via a conductor extending through a wall of the magazine to a location adjacent to an electrical contact of the first hemostatic clip.

The present invention is also directed to a combination hemostasis therapy device comprising a mechanical compression element and an energy delivery mechanism. The compression element deploys a hemostatic clip onto target tissue and the energy delivery mechanism delivers one of electrical and thermal energy to the hemostatic clip to cauterize the target tissue. The heating mechanism includes a conductor supplying energy to the hemostatic clip. The combination device further comprises a magazine containing a plurality of hemostatic clips arranged in a chain. The conductor supplies energy to a proximal most one of the clips for transmission therethrough to an adjacent clip. The conductor may extend through a wall of the magazine to a location adjacent to a distal most one of the clips. The heating device may deliver energy directly to a distal portion of the combination device. The distal portion of the combination device may deliver one of electrical, thermal and optical energy to the target tissue.

The present invention has been described with reference to specific exemplary embodiments. Those skilled in the art will understand that changes may be made in details, particularly in matters of shape, size, material and arrangement of parts without departing from the teaching of the invention. For example, different mechanisms for deploying the hemostatic clips may be used. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. An apparatus, comprising:
    a hemostatic clip assembly comprising a plurality of hemostatic clips, a first one of the hemostatic clips having a tissue clamp movable between a tissue receiving configuration and a tissue clamping configuration, each of the hemostatic clips including an insulating layer along an inner surface for conductive isolation from other hemostatic clips;
    a magazine receiving the hemostatic clips in a chain therein, with each clip coupling to an adjacent clip;
    a deployment mechanism deploying a distal most one of the clips onto target tissue, the distal most one of the clips remaining on the chain until deployment; and
    a cautery apparatus heating only the distal most one of the clips to cauterize the target tissue.

2. The apparatus according to claim 1, wherein the cautery apparatus comprises an electric element transmitting electric energy to the distal most clip.

3. The apparatus according to claim 1, wherein the deployment mechanism is coupled to a user operated actuator commanding deployment of the distal most clip.

4. The apparatus according to claim 1, wherein the cautery element operates concurrently with the deployment mechanism to provide combination therapy.

5. The apparatus according to claim 1, wherein the electric element extends through the magazine to couple to the distal most clip.

6. A device, comprising:
    a mechanical compression element deploying a hemostatic clip onto target tissue, the hemostatic clip including an insulating layer along an inner surface for conductive isolation from a further proximally disposed hemostatic clip;
    a magazine containing therein the hemostatic clip and a plurality of further hemostatic clips arranged in a chain, the hemostatic clip coupling to an adjacent further hemostatic clip and remaining on the chain until deployment; and
    a heating mechanism heating only the hemostatic clip to cauterize the target tissue.

7. The device according to claim 6, wherein the heating mechanism includes a conductor supplying electric energy to the hemostatic clip.

8. The device according to claim 6, wherein the heating mechanism includes a conductor extending through a wall of the magazine to a location adjacent to a distal most one of the clips.

9. The device according to claim 6, further comprising a shaft housing the mechanical compression element, the heating element, and the heated hemostatic clip, the shaft being dimensioned to fit through a working channel of an endoscope.

* * * * *